United States Patent [19]
Bornhop

[11] Patent Number: 5,325,170
[45] Date of Patent: Jun. 28, 1994

[54] LASER-BASED REFRACTIVE INDEX DETECTOR USING BACKSCATTER

[75] Inventor: Darryl J. Bornhop, Truckee, Calif.

[73] Assignee: Thermo Instrument Systems Inc., Santa Fe, N. Mex.

[21] Appl. No.: 73,788

[22] Filed: Jun. 8, 1993

Related U.S. Application Data

[63] Continuation of Ser. No. 531,999, May 31, 1990, abandoned.

[51] Int. Cl.⁵ .......................................... G01N 21/41
[52] U.S. Cl. ........................................ 356/128; 356/361
[58] Field of Search ............................. 356/128–137, 356/73.1, 338, 342, 344, 317, 318, 326, 328, 361, 357

[56] References Cited

U.S. PATENT DOCUMENTS

| | | | |
|---|---|---|---|
| 4,197,007 | 4/1980 | Costa et al. | 356/73.1 |
| 4,361,402 | 11/1982 | Costa | 356/128 |
| 4,515,475 | 5/1985 | Payne et al. | 356/73.1 |
| 4,660,974 | 4/1987 | Machler et al. | 356/128 |
| 4,673,299 | 6/1987 | Dakin | 356/73.1 |
| 5,168,325 | 12/1992 | Yoder-Short | 356/361 |

FOREIGN PATENT DOCUMENTS 2537280  6/1984  France ........................ 356/73.1

*Primary Examiner*—Richard A. Rosenberger
*Assistant Examiner*—Hoa Q. Pham
*Attorney, Agent, or Firm*—Killworth, Gottman, Hagan & Schaeff

[57] ABSTRACT

A refractive index detector for use in fluid phase separation techniques such as liquid chromatography and capillary electrophoresis uses a laser beam incident on a capillary tube held in a fixture. The laser beam is refracted and reflected (backscattered) from the capillary tube surface and its contents back to a photodetector located adjacent to the laser source. Tilting of the capillary tube relative to the laser beam axis produces a diffraction pattern on the photodetector, allowing detection of refractive index. Other embodiments use a split incident laser beam part of which is incident on a reference photodetector, or use a split beam which is incident on two capillary tubes juxtaposed to one another. In this case a photodetector is provided for the portion of the beam reflected from each capillary tube. The system may also be used for detecting temperature and pressure of the fluid inside the capillary tubes.

14 Claims, 3 Drawing Sheets

LASER-BASED REFRACTIVE INDEX DETECTOR USING BACKSCATTER

This is a continuation of application Ser. No. 07/531,999 filed May 31, 1990 now abandoned.

BACKGROUND OF THE INVENTION

1. Field of the Invention

This invention relates to detecting the refractive index of a fluid sample. More specifically, the invention relates to a method and device using a laser beam reflected from a capillary tube holding a fluid to determine the refractive index of the fluid.

2. Description of the Prior Art

It is known in the art (see FIG. 1) to measure refractive index using a beam 4 emitted from laser 6 which is focused by lens 8 on a micrometer diameter capillary tube 10 as described in "Simple Nanoliter Refractive Index Detector", Darryl J. Bornhop, et al., 58 *Analytical Chemistry* pg. 504 (1986), and incorporated by reference herein. Incident laser beam 4 is diffracted by capillary tube 10. Refractive index measurements are made by a photodetector (D1) 12 measuring the intensity of laser beam 13 transmitted through capillary tube 10. A reference beam 14 is provided from laser beam 4 by beam splitter 15, and reference beam 14 is detected by reference photodetector (D2) 16 to compensate for intensity drift by the laser 6 by an operational amplifier 17 which subtracts common-mode laser noise from the refracted light. A digital volt meter (DVM) 18 records the signal. Such devices are used to test small volume samples in the nanoliter range.

A refractive index detector such as this is one of the few universal optical detectors available for fluid samples. However, these detectors tend to be either very expensive to manufacture or difficult to adjust. Typically in these devices the laser beam is focused on the tube and passes through the tube to a detector which is on the far side of the tube from the laser source. This arrangement disadvantageously requires a lens to focus the laser beam off the center axis of the capillary tube and also requires a second reference beam from the same or a second laser. Thus this method requires careful optical alignment and is thus somewhat complex and relatively difficult to assemble. Also, it is difficult to use the prior art methods with a flow cell that has a thermal compensation feature such as an optical reference arm. Additionally the single pathlength limits the ultimate sensitivity of the device.

SUMMARY OF THE INVENTION

In accordance with the present invention, a refractive index measurement apparatus and method use an incident laser beam reflected (i.e., backscattered) from a tube back to a photodetector located adjacent to the laser source. By tilting the tube, which may be a capillary tube and is typically a conventional flow cell, an interference pattern is generated detectable by the photodetector resulting in a simple, reliable, and sensitive means of measuring refractive index of a fluid in the tube. No focusing lens is required. In one embodiment, a beam splitter generates a reference beam from the laser beam and the reference beam is measured by a second photodetector for reference purposes. In another embodiment, the laser beam is split and imaged on two individual capillary tubes, one of which contains a reference fluid and the second a sample fluid.

The optical path of the apparatus is easy to construct and align and does not require precise dimensionality. This method and apparatus are applicable to liquid chromatography detectors, capillary electrophoresis detectors, and fluid-phase separation detectors such as fluid injection analysis, high performance liquid chromatography detectors, preparative scale, high performance liquid chromatography, microbore high performance liquid chromatography, and capillary high performance liquid chromatography. The measurement of refractive index can also be used as a nondestructive non-evasive method to measure temperature or pressure of the fluid in the tube.

BRIEF DESCRIPTION OF THE DRAWINGS

Identical reference numerals in various figures denote similar structures.

DETAILED DESCRIPTION OF THE INVENTION

Figure 1:
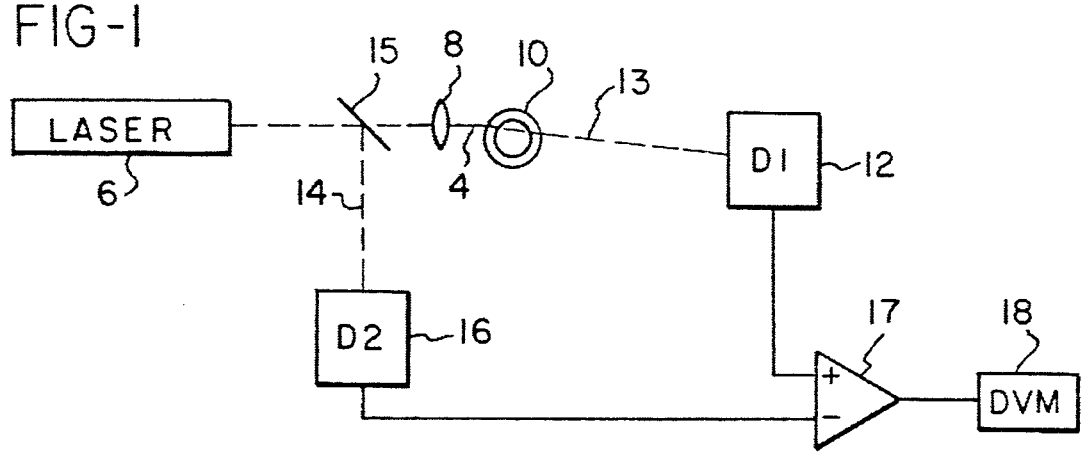
FIG. 1 shows a prior art refractive index measurement system.
Figure 2A:
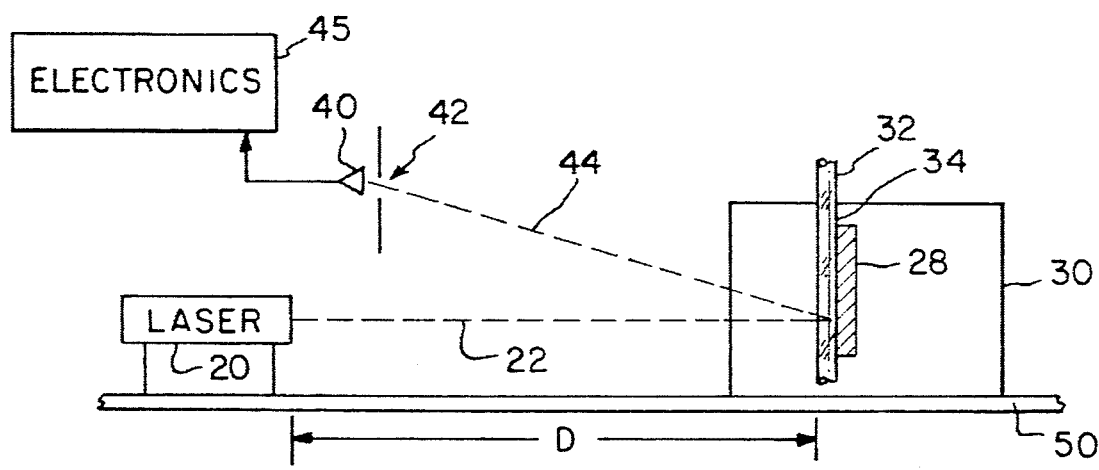
FIG. 2(a) shows a system in accordance with the invention.

As shown in FIG. 2(a), an apparatus in accordance with the invention includes a helium-neon (HeNe) laser 20. In one embodiment laser 20 is a commercially available model 05LHP141 laser from Melles Griot providing about 5 milliwats of power at 632.8 nm wavelength. Laser 20 emits a laser beam 22 of 0.8 millimeters in diameter. In other embodiments, any laser with a reasonable coherence length, i.e. capable of providing a parallel beam of reasonable length, may be used. Laser beam 22 passes through a front surface of conventional capillary tube 32. A conventional fixture 30 holds tube 32. A wall 34 of fixture 30 is covered with a black material so as to absorb light, thus acting as a beamstop to prevent reflections inside tube 32 from laser beam 22. Fixture 30 in one embodiment includes a groove formed in fixture 30 (i.e., an aluminum block) with tube 32 fastened into the groove by adhesive.

Capillary tube 32 in one embodiment is 530 micrometers inside diameter and 775 micrometers outside diameter and is conventional fused silica tubing supplied by Polymicro Technologies of Tucson, Arizona. In other versions, capillary tube 32 is 50 micrometers inside diameter up to 775 micrometers in inside diameter; other sizes are also in accordance with the invention. Tube 32, which conventionally has a polyimide plastic coating, may be modified by removing polyimide coating from the portion 34 of tube 32 around the entire circumference of tube 32 at the location at which incident laser beam 22 strikes tube 32. The polyimide plastic coating is removed by heating that portion of the tube in a flame, or by acid or by heat from an electrical discharge. Tube 32 is held in fixture 30 so that tube 32 is tilted with respect to the axis of incident laser beam 22.

As shown, laser beam 44 is reflected from tube 32 to a conventional photodetector 40. Tilting of tube 32 ensures that reflected laser beam 44 does not reenter laser 20. Immediately in front of photodetector 40 is a conventional optical slit 42 of width approximately 200 microns. Photodetector 40 is a conventional silicon photodiode, a photodiode array, or a multi-element charge coupled device image detector. In one embodiment photodetector 40 is a conventional silicon photodiode provided by United Detector Technology, Model FIL20V for detecting the red through infrared portion of the spectrum with enhanced detection and thus is matched with the output of helium-neon laser 20. In another embodiment a multielement detector is used for an extended linear detection range. The multielement detector, used without a slit, is a photodiode array such as the 512 element commercially available EG&G Reticon 512S, with the diodes spaced 25$\mu$ center-to-center and a diode width of 15$\mu$. Alternatively, a conventional CCD array is used. Other photodetectors are also in accordance with the invention.

The output of photodetector 40 is a current proportional to the amplitude of reflected laser light 44 incident on photodetector 40. Electronics circuitry 45 includes a conventional operational amplifier-based current to voltage converter (not shown) and circuitry providing amplification (not shown) of the converter output in the desired voltage range. Electronics 45 thus provide output signals in the form of a monitor voltage which is displayed on a digital volt meter (not shown) or by similar device, and a differential voltage which may be recorded and displayed by a strip chart recorder (not shown) showing the noise baseline and the voltage peaks. The system is conventionally mounted on a conventional optical bench 50.

The lateral position of reflected beam 44, i.e. the fringe pattern which is the reflective image, is modified by tilting fixture 30 and/or tube 32 within fixture 30. This tilting uses the curvature of tube 32 to focus the reflected beam 44 pattern on detector 40. Thus the reflected image is a set of light and dark alternating fringes (bright spots) which are wide in the center and narrower on either side of the center. Tilting of tube 32 focuses a particular one of these rectangular bright spots on detector 40. Thus slit 42 is smaller than the spacing between two adjacent bright spots in the fringe pattern so that only a portion of one bright spot is detected by detector 40 at any given time. As the position of the bright spot moves with the movement of tube 32, it is possible to monitor the intensity of the bright spot which thus provides a measurement of refractive index.

Tube 32 is aligned so that a small output voltage is measured by detector 40. That is, reflected beam 44 is manipulated so that as the refractive index changes the intensity of beam 44 through slit 42 increases. The relative position of tube 32, slit 42, and detector 40 are then fixed. As the refractive index of the fluid in tube 32 or a related property such as temperature or pressure changes, the position of the fringes in beam 44 shifts in space. The direction of the shift corresponds to the sign change in refractive index. As the position of the fringes changes, the amount of light reaching detector 40 changes. In one embodiment, a change in refractive index of $4.0^{-4}$ produces a change in detector 40 output from maximum intensity to null intensity, i.e., a shift of a bright spot from being on detector 40 to being off detector 40.

Absolute refractive index measurements are performed with a calibrated set of measurements; thus changes in refractive index are more easily measured than are absolute measurements. Large changes (exceeding 0.01) in refractive index are most easily measured with a multi-element detector because the fringes' position shifts significantly in space as described above. With a single slit the linear range of changes on refractive index is determined by spatial fringe shift and slit width.

Figure 2B:
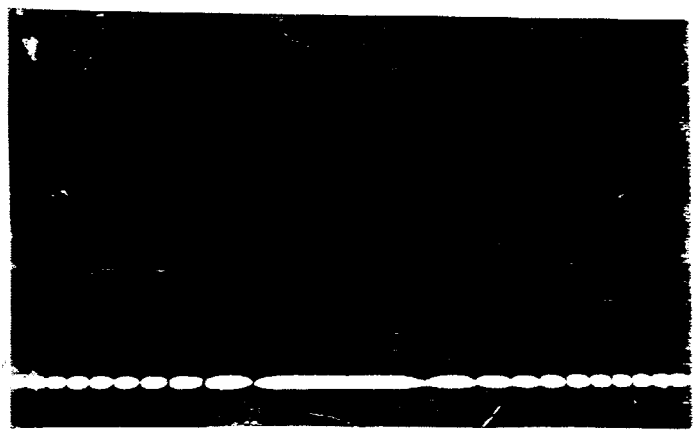
FIG. 2(b) shows a fringe pattern produced by the system of FIG. 2(a).

FIG. 2(b) shows a typical beam profile observed for a helium neon laser source incident on a capillary tube containing water at a distance D (see FIG. 2(a)) of 8.5 inches between the emitting end of laser 20 and capillary tube 32. This is the interference fringe pattern as discussed above.

It has been found by experimentation that typically a tilt of tube 32 of no more than 15° relative to the surface of optical bench 50 supporting laser 20 and fixture 30 provides optimum results. A tilt of 15° is sufficient to image the reflected pattern out of the plane of the source plane.

Figure 3:
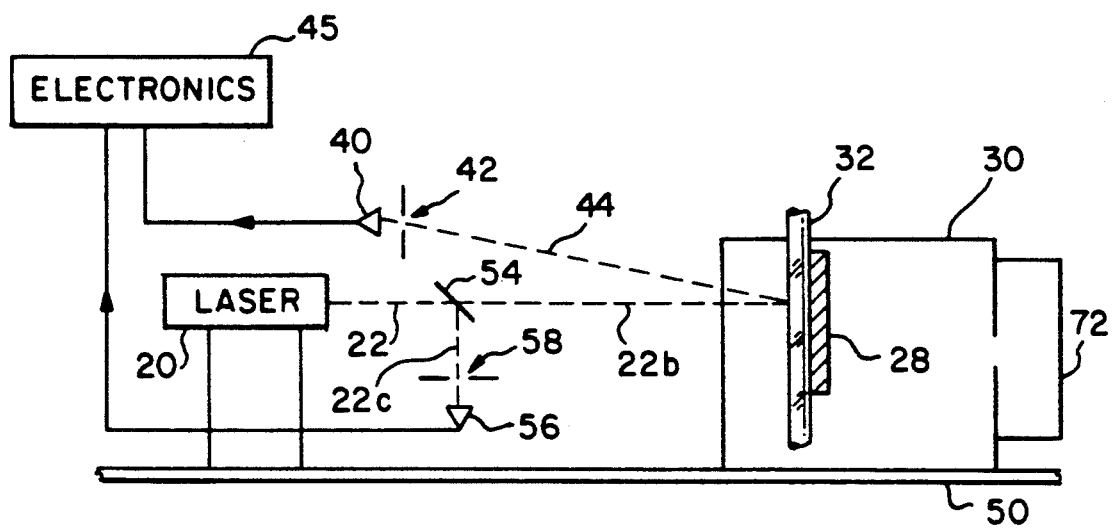
FIG. 3 shows a double beam system in accordance with the invention.

As shown in FIG. 3 another embodiment includes a conventional beam splitter 54 (such as a microscope slide) which splits laser beam 22 into two portions 22b, 22c. A first portion 22b is incident on capillary tube 32 and reflected back to detector 40 via slit 42. A second portion 22c of the split beam is directed to a reference detector 56 via slit 58. This second portion 22c allows compensation for thermal drift of the laser 20 output intensity, thus permitting measurement at low refractive index levels, i.e., very sensitive measurements of small changes in refractive index. The system uses a position measurement dependent on the ability to detect changes in intensity. As the intensity of the laser changes so will the amount of light received by the detector if no refractive index change occur. If the intensity of the beam changes, a false signal is produced. For the reference arm the beam intensity also changes so that a difference in intensity between a reference and sample arm is insensitive to beam intensity changes. In this embodiment, the electronics portion 45 is responsive to the difference between the output of detector 40 receiving the beam reflected from tube 32 and the output of reference detector 56. Electronics 45 are of the conventional "A-B circuit" type described below. Typically in both the embodiments of FIG. 2 and FIG. 3 a distance of approximately 8.5 inches (21.6 cm) is provided between the emitting end of laser 20 and capillary tube 32. This distance is illustrative and not limiting.

Since it is known that index of refraction is a function of temperature and also of pressure, the above described apparatus may be used to measure both temperature and pressure, i.e. as a temperature or pressure sensor. As the temperature of the fluid changes, so will the refractive index. This change in refractive index produces a fringe pattern positional shift which is detected as described above.

Figure 4A:
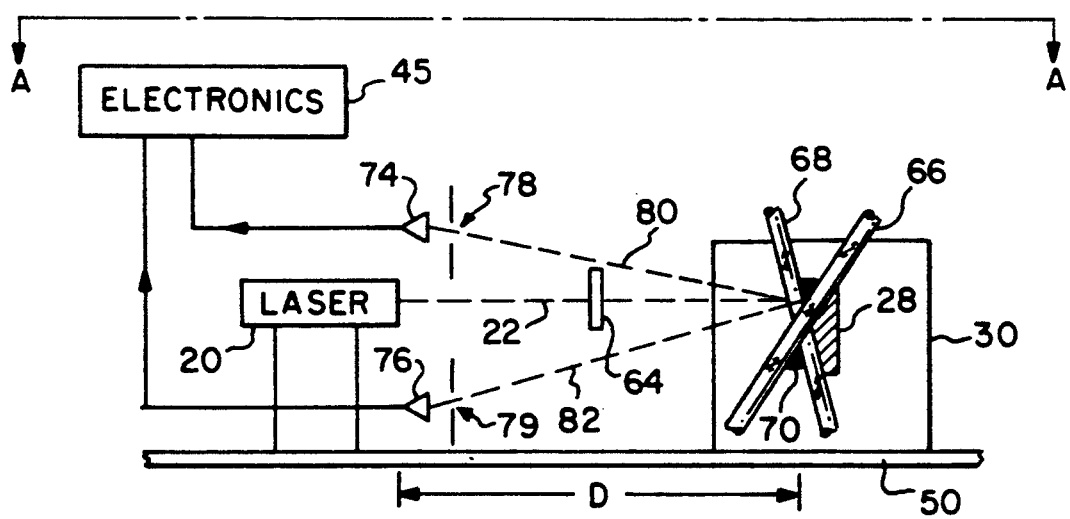
FIG. 4(a), 4(b) show a system using two capillary tubes in accordance with the invention.

Another system in accordance with the invention is shown in FIG. 4(a). Emitted beam 22 from helium-neon laser 20 is directed onto a conventional calcite beam displacer 64 which is 19 millimeters in length and 5 mm square. Calcite beam displacer 64 provides two parallel beams each of diameter 0.8 mm which are spaced apart (center-to-center) by 2 mm and which are directed respectively onto two independent capillary tubes 66, 68. In one embodiment, the two parallel beams are reflected onto capillaries 66, 68 by a mirror (not shown) so as to provide a more compact optical path. Both capillaries 66, 68 are mounted in fixture 30 which in one embodiment is an aluminum block with grooves formed in it to hold tubes 66, 68. Capillaries 66, 68 as shown are at an angle to one another so that in one embodiment capillary 66 is at an angle of +10° to the axis of incident laser beam 22 and capillary 68 is at an angle of −10° to the axis of beam 22.

Rear wall 28 of fixture 30 is coated with a black substance as described above to act as a laser beam stop. Capillaries 66, 68 are fixed together in fixture 30 by an environmental matching adhesive 70, i.e. an epoxy adhesive, and in one embodiment both tubes 66, 68 are immersed in a refractive index matching temperature controlling fluid (not shown) to keep both tubes 66, 68 at the same temperature so that temperature effects do not influence the measured angle of refraction. This embodiment requires that fixture 30 have a transparent front window (not shown) and hold the fluid inside, with the front window also matching the refractive index of tubes 66, 68. Fixture 30 is attached to a conventional Peltier thermoelectric cooler (not shown) which provides temperature control to within, for instance, one-half degree Centigrade.

In the embodiment shown in FIG. 3 Peltier cooler 72 is attached to fixture 30 which is an aluminum block with tube 32 partly exposed to the ambient air. No temperature controlling fluid is used in this embodiment. A Peltier cooler may be similarly attached to fixture 30 in the embodiments of FIG. 2(a) and 4(a).

Two photodetectors 74, 76 are provided, one on either side of laser 20. Each photodetector 74, 76 is immediately behind a conventional slit, respectively 78, 79, which are each a spatial filter. The width of each slit 78, 79 is about 50 to 200 μm. Thus each photodetector 74, 76 respectively receives light 80, 82 reflected from one of the two capillaries 66, 68. This system allows two different fluids to be provided in capillaries 66, 68. In one version, for chromatography the first capillary 66 contains a sample in an elution solvent, The second capillary 68 contains only the elution solvent. Thus a differential result of the reflection, i.e. index of refraction, of the sample versus the solvent is obtained. Tubes 66, 68 are mounted in fixture 30 so as to be tilted relative to the axis of incident laser beam 22 thus focusing particular portions of the reflected image 80, 82 back on detectors 74, 76. Thus one may monitor the intensity of the reflection 80, 82 by the position of particular bright spots as focused on photodetectors 74, 76.

Figure 4B:
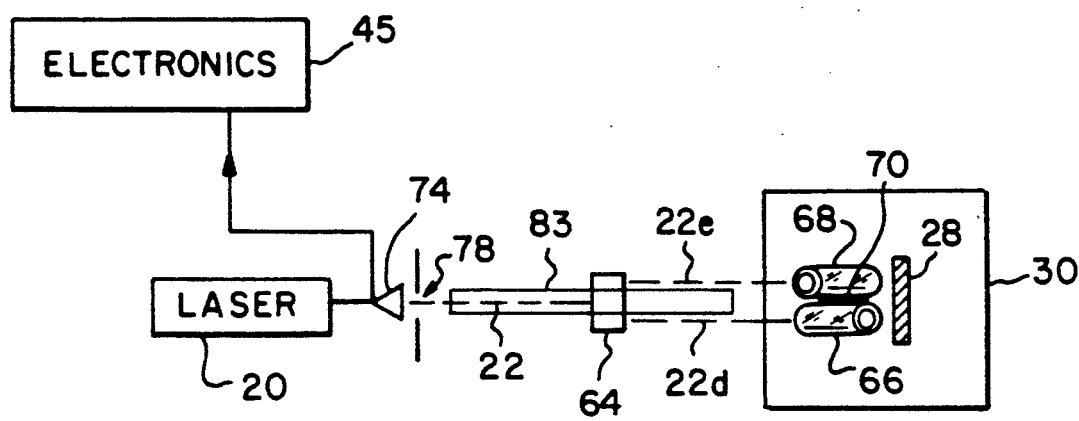

The system of FIG. 4(a) is shown in top view (along reference line A—A) in FIG. 4(b). Here parallel beams 22c, 22d as they emerge from beam splitter 64 are shown as incident on capillary tubes 66, 68.

Figure 5:
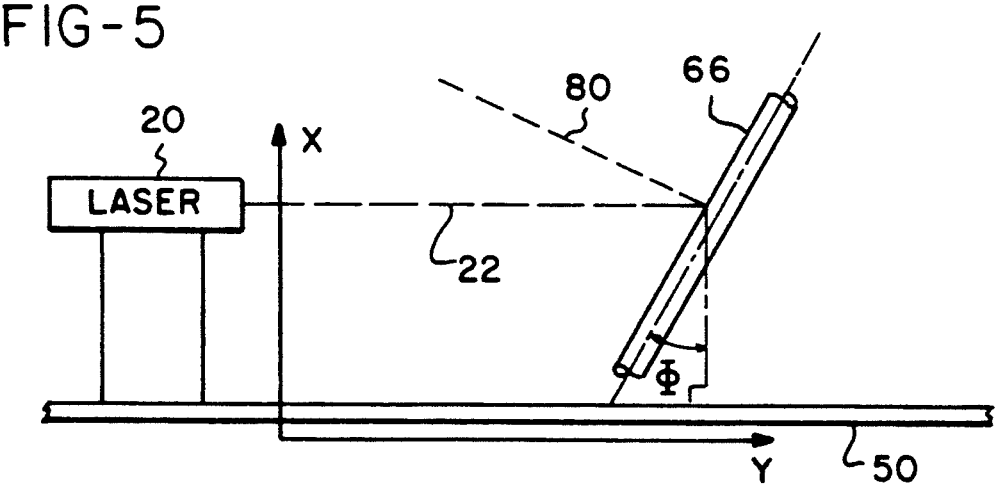
FIG. 5 shows the orientation of a capillary tube in accordance with the invention.

FIG. 5 shows for the system of FIGS. 4(a) and 4(b) how the angle Φ determines the position (height X) that the fringe pattern, i.e. the reflected laser beam 80, returns to relative to laser 20. Height X is relative to an axis of incident laser beam 22. As shown, the right angle indicates a capillary tube 66 which is at right angles to the axis of incident laser beam 22. The Y axis represents the surface of optical bench 50 on which laser 20 and tube 66 as held in fixture 30 (not shown) are mounted. Thus reflected beam 80 is directed above laser 20, i.e. to upper photocell 74 (not shown in FIG. 5). A negative value of angle Φ is used for the second capillary tube (not shown) to direct the reflected pattern below laser 20, i.e. to the lower photocell 76 in FIG. 4(a).

In the embodiment shown in FIGS. 4(a) and 4(b) electronics 45 includes a conventional operational amplifier-based "A-B circuit". This includes a commercially available instrumentation amplifier (not shown) which obtains inputs of voltage A and voltage B as converted from the currents generated by respectively photodetectors 74, 76. The amplifier produces an output current proportional to the difference between voltage A and voltage B. In this embodiment, it is also useful to include a light baffle 83 (as in FIG. 4(b)) to separate the two parallel incident light beams 22d, 22e and prevent crosstalk therebetween. Light baffle 83 extends from the front surface of fixture 30 to near photodetectors 74, 76.

The above description is illustrative and not limiting. Further modifications will be apparent to one of ordinary skill in the art in light of the disclosure and appended claims.

I claim:

1. A refractive index detector comprising:
    a first capillary tube for containing a fluid whose refractive index is to be determined;
    a laser light source for emitting an unfocused laser beam onto a sidewall of said first capillary tube, the width of said laser beam being substantially equal to or greater than the diameter of said first capillary tube;
    a first photodetector adjacent to said laser light source for receiving those portions of the laser light backscattered from said first capillary tube and fluid contained therein and providing a first output signal indicative of the intensity of the laser light received by said first photodetector; and
    means communicating with said first photodetector for monitoring said first output signal as a measure of the refractive index of said fluid.

2. The refractive index detector of claim 1 further comprising a slit for limiting light received by the first photodetector.

3. The refractive index detector of claim 1 further comprising a fixture in which said first capillary tube is mounted, and a beam stop adjacent to a surface of said first capillary tube remote from a surface of said first capillary tube on which said laser beam is incident.

4. The refractive index detector of claim 3 further comprising means for controlling a temperature of said first capillary tube, wherein said means for controlling is attached to said fixture.

5. The refractive index detector of claim 1 further comprising:
    a beam splitter for splitting said laser beam emitted from the laser light source;
    a second photodetector for receiving a portion of the beam split by said beam splitter; and
    means for comparing a signal provided by the first photodetector with a signal provided by the second photodetector.

6. The refractive index detector of claim 1 further comprising means for tilting said first capillary tube relative to an axis of said emitted laser beam.

7. The refractive index detector of claim 1 wherein said first photodetector comprises a linear array of photodetecting elements.

8. A refractive index detector comprising:
    a first capillary tube for containing a fluid whose refractive index is to be determined;
    a laser light source for emitting a laser beam onto a sidewall of said first capillary tube;
    a beam displacer for displacing said laser beam emitted by said laser light source into at least two parallel beams;
    a second capillary tube for containing a reference fluid juxtaposed and at an angle to said first capillary tube and upon which one of said laser beams is incident;

a first photodetector adjacent to said laser light source for receiving those portions of the laser light backscattered from said first capillary tube and fluid contained therein and providing a first output signal indicative of the intensity of the laser light received by said first photodetector;

a second photodetector for detecting the laser light backscattered from said second capillary tube and fluid contained therein and providing a second output signal indicative of the intensity of the laser light received by said second photodetector; and means communicating with said first and second photodetectors for comparing said first and second output signals as a measure of the refractive index of said fluid in said first capillary tube.

9. A method for measuring refractive index of a fluid comprising the steps of:

providing a first capillary tube containing a fluid whose refractive index is to be determined;

emitting an unfocused laser beam onto a sidewall of said first capillary tube, the width of said laser beam being substantially equal to or greater than the diameter of said first capillary tube;

detecting those portions of the laser light backscattered from said first capillary tube and fluid contained therein with a first photodetector and providing a first output signal indicative of the intensity of the laser light received by said first photodetector; and monitoring said first output signal as a measure of the refractive index of said fluid in said first capillary tube.

10. The method of claim 9 further comprising the steps of:

splitting said laser beam into at least two portions and directing a first portion onto said first capillary tube; measuring an intensity of a second portion of the beam with a second photodetector which provides a second output signal; and comparing said first output signal provided by said first photodetector with said second output signal provided by said second photodetector.

11. The method of claim 9 further comprising the step of converting said first output signal into a measurement of a pressure of said fluid in said first capillary tube.

12. The method of claim 9 further comprising the step of converting said first output signal into a measurement of a temperature of said fluid in said first capillary tube.

13. The method of claim 9 further comprising the step of tilting said first capillary tube relative to an axis of the laser beam.

14. A method of measuring refractive index of a fluid comprising the steps of:

providing a first capillary tube containing a fluid whose refractive index is to be determined and a second capillary tube containing a reference fluid;

splitting an emitted laser beam into two portions and directing a first portion onto a sidewall of said first capillary tube and a second portion onto a sidewall of said second capillary tube;

detecting those portions of the laser light backscattered from said first and second capillary tubes and the fluids contained therein with first and second photodetectors;

providing a first output signal indicative of the intensity of the laser light received by said first photodetector and a second output signal indicative of the intensity of the laser light received by said second photodetector; and comparing said first and second output signals as a measure of the refractive index of said fluid in said first capillary tube.

* * * * *